(12) United States Patent
Kihara et al.

(10) Patent No.: US 6,579,265 B1
(45) Date of Patent: Jun. 17, 2003

(54) ARTIFICIAL KIDNEY AND AN INSERTION GUIDE USED THEREIN

(75) Inventors: Kazuhiko Kihara, Kanagawa (JP); Akio Yamada, Tokyo (JP)

(73) Assignee: Hospal AG (CH)

( * ) Notice: Subject to any disclaimer, the term of this patent is extended or adjusted under 35 U.S.C. 154(b) by 26 days.

(21) Appl. No.: 09/786,509

(22) PCT Filed: Jul. 6, 2000

(86) PCT No.: PCT/IB00/00929

§ 371 (c)(1),
(2), (4) Date: Jun. 1, 2001

(87) PCT Pub. No.: WO01/03754

PCT Pub. Date: Jan. 18, 2001

(30) Foreign Application Priority Data

Jul. 7, 1999 (JP) ............................................. 11-193704

(51) Int. Cl.[7] .............................. A61M 1/00; A61M 5/32

(52) U.S. Cl. ............................. 604/174; 604/27; 604/29

(58) Field of Search ............................... 604/27, 29, 48, 604/93.01, 174, 179, 890.1, 896.1, 131, 288.01, 288.02, 288.04, 272, 273, 274, 264, 115, 117; 128/6, 26

(56) References Cited

U.S. PATENT DOCUMENTS

| 3,021,842 A | | 2/1962 | Flood ......................... 128/215 |
| 4,350,157 A | * | 9/1982 | Hoffa ......................... 128/899 |
| 4,679,553 A | * | 7/1987 | Proulx et al. ................ 128/846 |
| 4,822,341 A | * | 4/1989 | Colone ........................ 604/175 |
| 4,892,518 A | * | 1/1990 | Cupp et al. .................. 137/855 |
| 6,090,048 A | * | 7/2000 | Hertz et al. .................. 600/485 |
| 6,153,109 A | * | 11/2000 | Krivitski ..................... 210/646 |

FOREIGN PATENT DOCUMENTS

| EP | 0 318 358 | 5/1989 |
| GB | 2 143 134 A | 2/1985 |

* cited by examiner

Primary Examiner—Edward K. Look
Assistant Examiner—John K. Fristoe, Jr.
(74) Attorney, Agent, or Firm—Finnegan, Henderson, Farabow, Garrett & Dunner, L.L.P.

(57) ABSTRACT

An insertion guide is used for inserting an arterial needle, which takes blood out from the body, and a venous needle, which returns purified blood into the body, into one or two fistulae formed in a vein running beneath the skin of the arm. The insertion guide may include a holder having an arterial guide hole, which guides the arterial needle downwards at an incline from the shoulder side to the wrist side relative to the fistula, and a venous guide hole, which guides the venous needle downwards at an incline from the wrist side to the shoulder side relative to the fistula.

16 Claims, 11 Drawing Sheets

ARTIFICIAL KIDNEY AND AN INSERTION GUIDE USED THEREIN

BACKGROUND

1. Field of the Invention

The present invention relates to an artificial kidney which allows purification of the blood in places such as the home or a travel destination, without imposing a particularly great burden on daily life, and without the need for patients suffering from renal insufficiency to attend hospital, and it relates to an insertion guide used therein.

2. Description of Related Art

It has been predicted that by the year 2000 there will be 1,000,000 patients suffering from renal insufficiency around the world, 200,000 of them in Japan alone.

Methods of therapy which are known at the present time include, by way of example, artificial dialysis, kidney transplant and continuous ambulant peritoneal dialysis, abbreviated to CAPD, in which dialysis is carried out using a membrane.

However, CAPD entails a high risk of inducing complications which have a poor prognosis such as sclerotic peritonitis due to bacteria which invade the abdominal cavity from the tube system. Also, although the kidney bank system is becoming more widespread, and kidney transplants are the most common form of organ transplant, the number of registered donors nevertheless falls far short of the number of aspirant patients. The majority of patients with renal insufficiency therefore have to rely on artificial dialysis.

In artificial dialysis, blood is extracted from an artery via a tube, the blood is led into a dialysis device known as a dialyzer, where it is purified, and the purified blood is put back into the body.

The dialyzer is provided on the inside with a dialysis membrane formed from a flat membrane, hollow fibres or the like, and is arranged in such a way that, when the blood flows through it, waste materials in the blood pass through the dialysis membrane and diffuse into a dialysis fluid which flows on the outside, and thus the contaminated dialysis fluid is discarded and the constituents of the now cleansed blood are adjusted before it is put back into a vein.

In this case, the blood is supplied to the artificial kidney at 200 cc/min, but, even so, it requires about 5 to 6 hours to purify the blood of the whole body.

Moreover, such dialysis has to be carried out at a frequency of 3 times a week, which is to say about once every 2 days, and the time constraints of dialysis impose a considerable burden on the daily lives of patients and substantially curtail the social activities of patients.

Artificial kidneys which allow dialysis in the home and elsewhere have therefore also been proposed, but some 150 to 200 liters of dialysis fluid is required in a single dialysis in order to continuously replace the contaminated dialysis fluid in the dialysis device with fresh fluid, and artificial kidneys have been of a large size. Also, the patient has obviously not been able to move away from the bed while receiving dialysis.

In healthy individuals, on the other hand, about 180 liters of blood are filtered by the glomeruli in the kidneys within 24 hours, of which between 1 and 2% is discharged outside the body and the remaining 98 to 99 per cent is reabsorbed. Here, the amount of filtration by the glomeruli is 125 cc/min, while the amount discharged outside the body is 2 cc/min.

Now, if the blood is led into a filtration device, an aqueous fraction including waste materials extracted and excreted at 2 cc/min, and a fresh replenishing fluid mixed with the blood from which the waste materials have been eliminated and made to flow back into the body at 2 cc/min, then the amount discharged outside the body will be on the same level as in a healthy individual, and 2 cc will be purified every minute, but the blood of dialysis patients contains large amounts of urea and other unwanted waste materials, and requires an elimination level of at least 10 times this.

A purification rate of 20 cc/min should be achieved in order to satisfy this requirement, it is sufficient to excrete 20 cc/min of the water fraction (initial urine) containing waste materials obtained by the filtration of the blood, and to put back 20 cc/min of fresh replenishing fluid, and filtration devices with such a capacity can now be reduced to a size such that they are portable.

However, this method requires 1.2 liters per hour, or approximately 30 liters per 24 hours, of fresh replenishing fluid, and, since the amount of replenishing fluid used is excessive, portability cannot be extended to the replenishing fluid even if the filtration device is rendered portable, and thus it cannot be employed in portable artificial kidneys, in addition to which it is still inconvenient even if put to use in the home.

Also, when blood is purified using an artificial kidney, the system is arranged such that the blood is made to flow into a circulatory system outside the body, where it is purified, and is then made to flow back into the body by the insertion of an arterial needle and a venous needle into a fistula formed in the arm.

Further, when the blood is purified in a place such as the home, the needles have to be inserted by the individual him or herself since there are no dedicated staff, and even individuals who are not skilled at performing the insertion have to be given an ability to insert the needles to a certain degree since dexterity of insertion affects the life of the fistula.

Thus, the technical problems for the present invention are, firstly, to provide an artificial kidney which does not require a large amount of dialysis fluid or replenishing fluid, and with which the blood can be purified even in places such as the home and travel destinations, and secondly to provide an insertion guide which allows anybody at all to easily insert the needles into the fistula formed in the arm when such an artificial kidney is used.

SUMMARY

In above mentioned problem, an artificial kidney according to the present invention is characterized in that a circulation system outside the body connected to the circulation system inside the body is provided with a filtration device which filters blood taken from inside the body and extracts, in the form of initial urine, a water fraction containing waste materials; a distillation device which distills the above mentioned initial urine and recovers distilled water, and discharges the initial urine in which the waste materials have been concentrated; and a purified blood mixing device which uses the above mentioned distilled water to dilute a concentrated replenishing fluid to a predetermined concentration, and mixes it with the blood from which initial urine has been eliminated in the above mentioned filtration device and returns the mixture into the body.

When the artificial kidney according to the present invention is employed, the water fraction (initial urine) containing waste materials is extracted as a filtrate at about 30 cc/min by taking blood at about 125 cc/min from inside the body and filtering it in a filtration device.

Also, by using the distillation device to perform distillation and not discharging the filtrate straight away, 28 cc/min of distilled water is recovered, and the initial urine in which waste materials have been concentrated is discharged at 2 cc/min.

Also, approximately 124 cc/min of purified blood, obtained by mixing approximately 1 cc/min of a concentrated replenishing fluid diluted with 28 cc/min of distilled water, and 95 cc/min of blood from which initial urine has been eliminated in the filtering device, is returned to the body.

In this way, purification of the blood is possible with only a small amount of concentrated replenishing fluid since distilled water obtained from the distillation of initial urine is reused, and this distilled water is used to dilute the concentrated replenishing solution.

At this time, if a commercially available dialysis source fluid which has been concentrated 35 times is used as the concentrated replenishing solution, then the requisite amount of dialysis source fluid is 28/35=about 0.8 cc/min, and is 28×60×24/35=1152 cc even assuming that the artificial kidney is made portable and the blood is purified continuously over 24 hours, and thus, by way of example, it is sufficient to replace a bag containing 300 cc every 5 to 6 hours.

In this way, given that the blood filtration rate inside the body is 28 cc/min, it is possible to maintain a kidney performance approximately 25% of the filtration rate of 125 cc/min of healthy individuals, and this is believed to be on the same level as the kidney performance in patients undergoing dialysis in institutions such as dialysis centers attached to university hospitals and the like.

Further, in order to overcome the second problem, the insertion guide according to the present invention disclosed in claims 7 to 12 is characterized in that it is an insertion guide for inserting an arterial needle which takes blood out from the body, and a venous needle which returns purified blood into the body, into one or two fistulae formed in a vein running beneath the skin of the arm: said insertion guide has formed in it an arterial guide hole which guides the above mentioned arterial needle downwards at an incline from the shoulder side to the wrist side relative to the above mentioned fistula, and a venous guide hole which guides the above mentioned venous needle downwards at an incline from the wrist side to the shoulder side relative to the above mentioned fistula, running through a holder fitted to the arm in such a way as to cover the above mentioned fistula.

When the insertion guide according to the present invention is employed, once the holder has been fitted to the arm and the arterial needle and the venous needle have been poked through their respective guide holes, the arterial needle is inserted by being guided downwards at an incline from the shoulder side to the wrist side relative to the fistula, while the venous needle is inserted by being guided downwards at an incline from the wrist side to the shoulder side relative to the fistula.

The needles can be inserted simply and under more or less the same conditions whoever inserts them, without any lateral shaking, since they are guided only in the longitudinal direction by the guide holes, both when they are being put in and when they are being withdrawn.

BRIEF DESCRIPTION OF THE DRAWINGS

Modes of embodiment of the present invention are described in greater detail below with reference to the appended drawings, in which.

DESCRIPTION OF EXEMPLARY EMBODIMENTS

Figure 1:
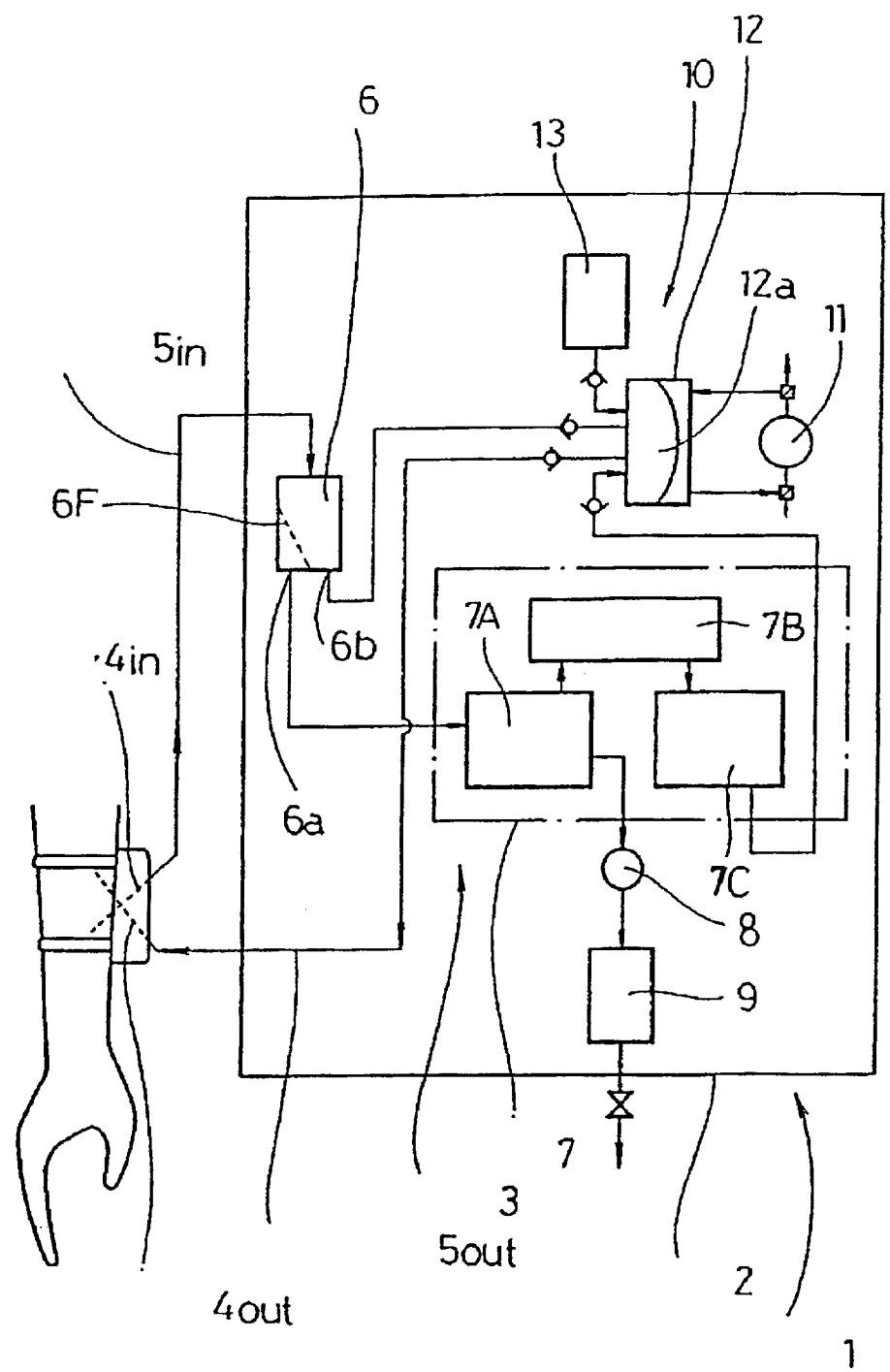
FIG. 1 represents a fluid circuit diagram showing an artificial kidney according to the present invention.
Figure 2:
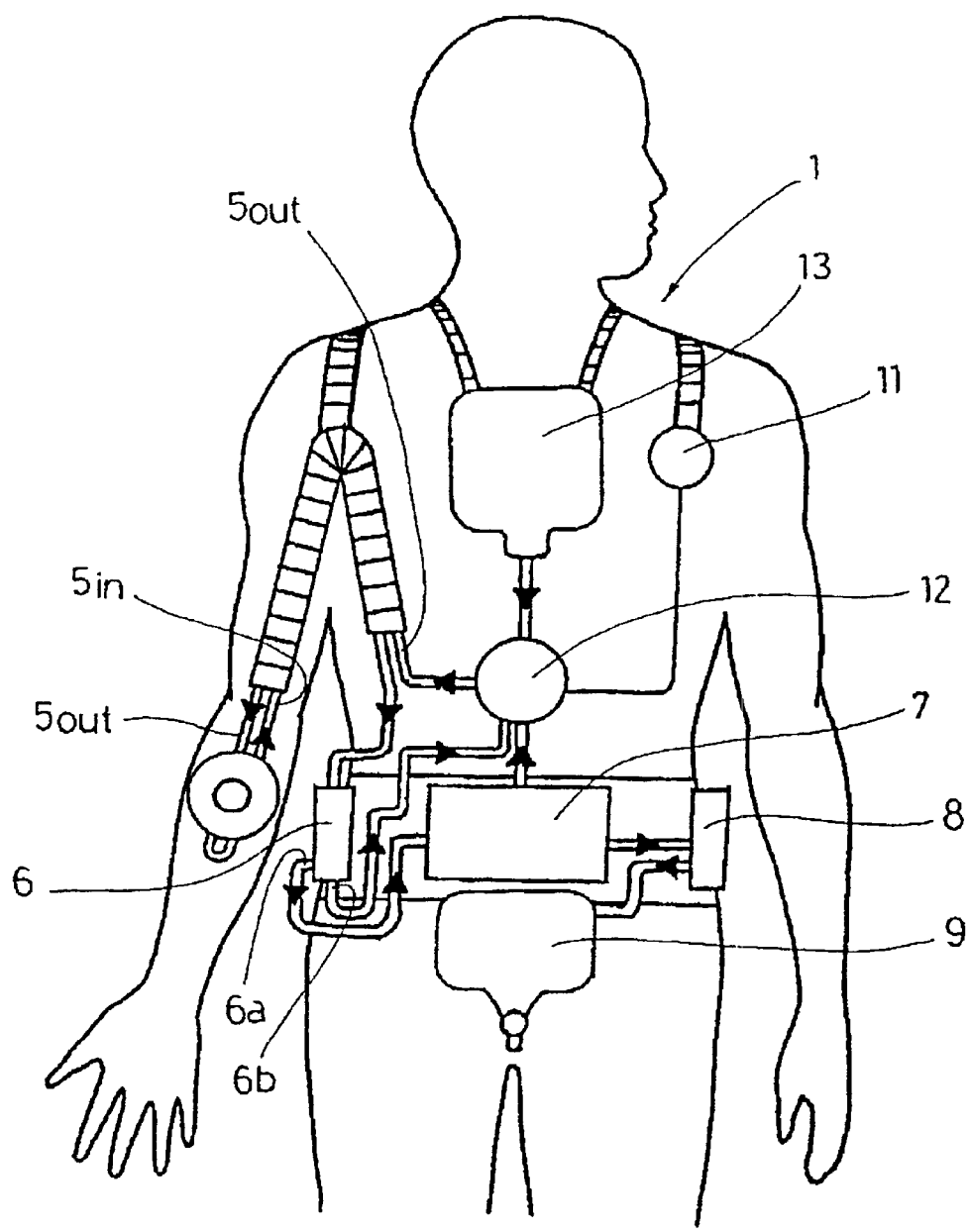
FIG. 2 represents the artificial kidney in operation.
Figure 3:
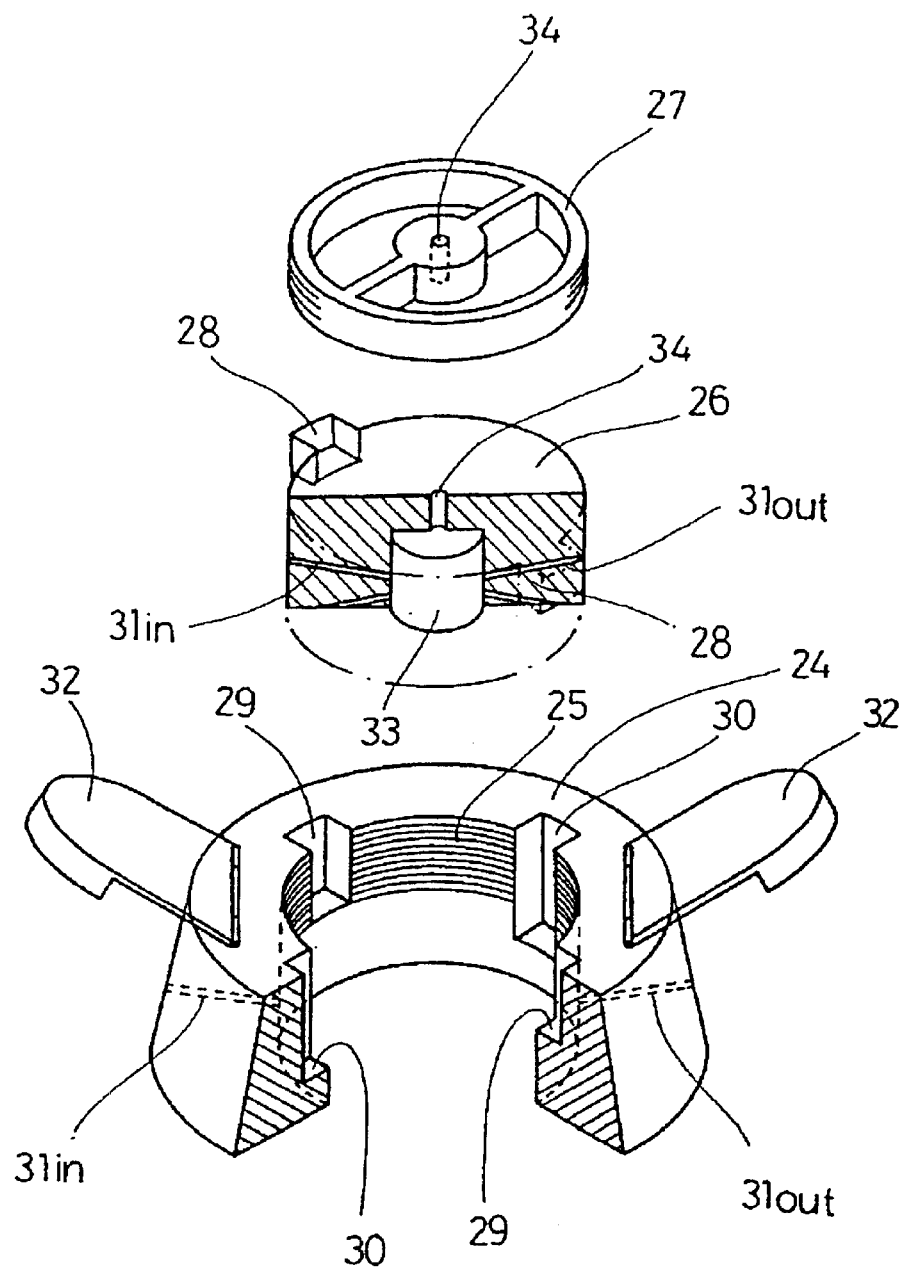
FIG. 3 represents an exploded assembly diagram showing an insertion guide used therein.
Figure 4:
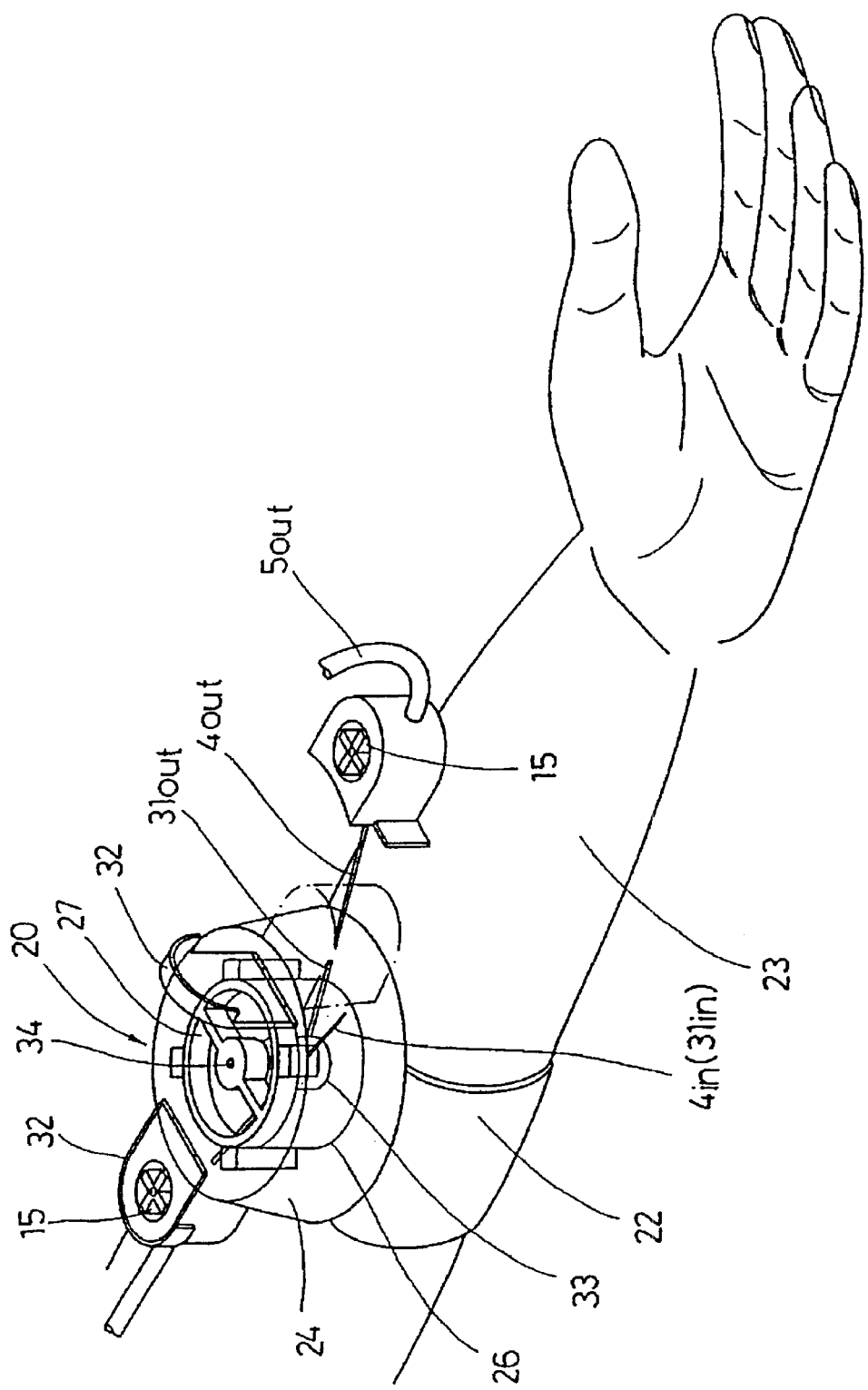
FIG. 4 represents the insertion guide fitted to the arm.
Figure 5A:
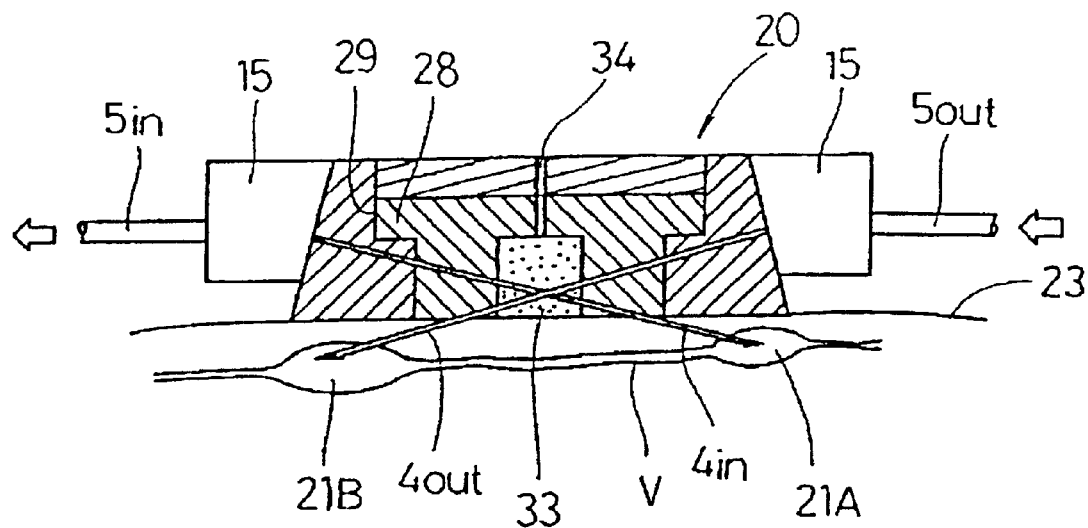
FIG. 5 is an explanatory figure showing how it is used.
Figure 5B:
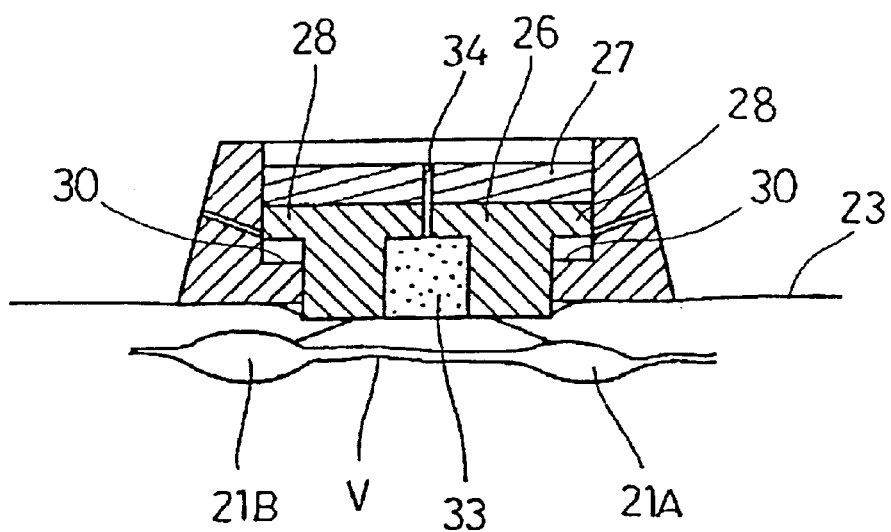
Figure 6:
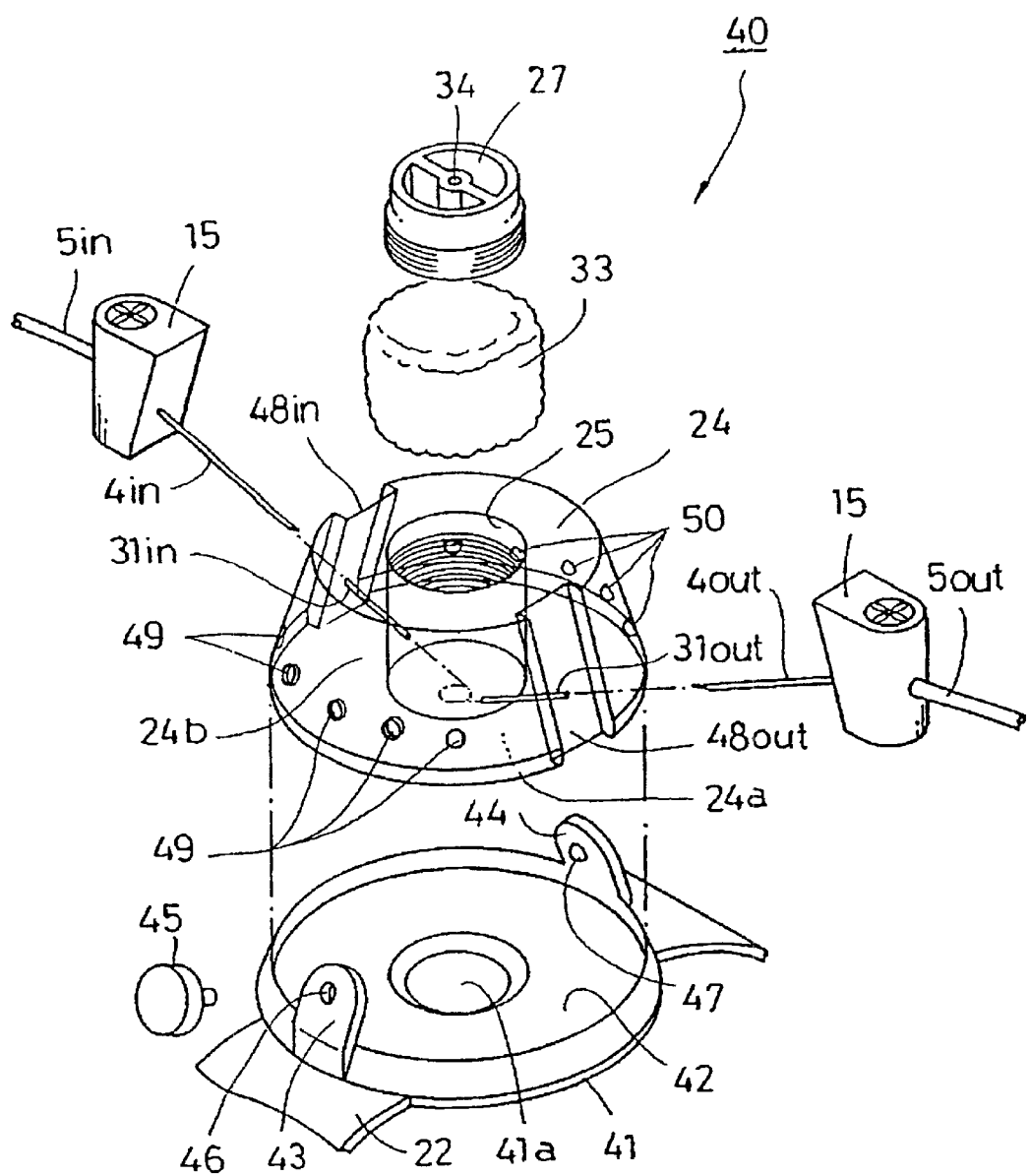
FIG. 6 represents an exploded assembly diagram showing another mode of embodiment of the insertion guide.
Figure 7:
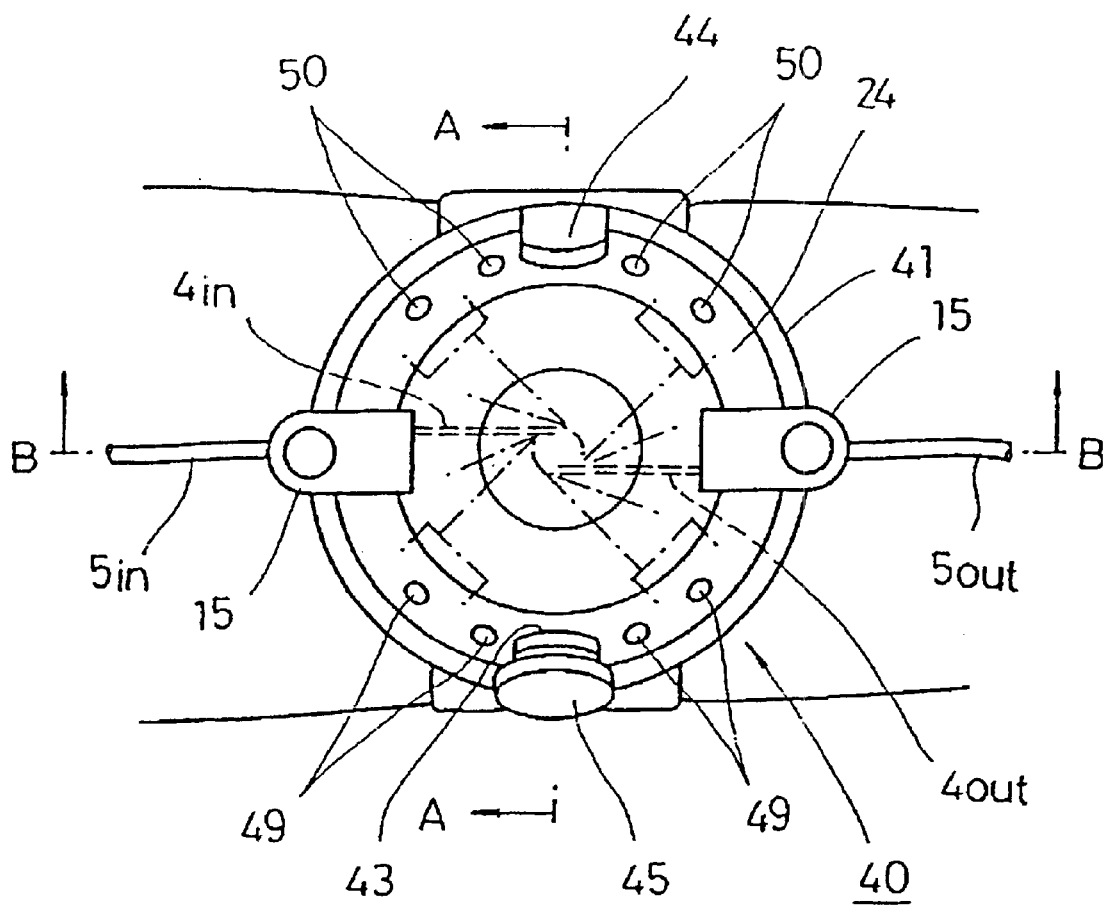
FIG. 7 represents a plan view thereof.
Figure 8:
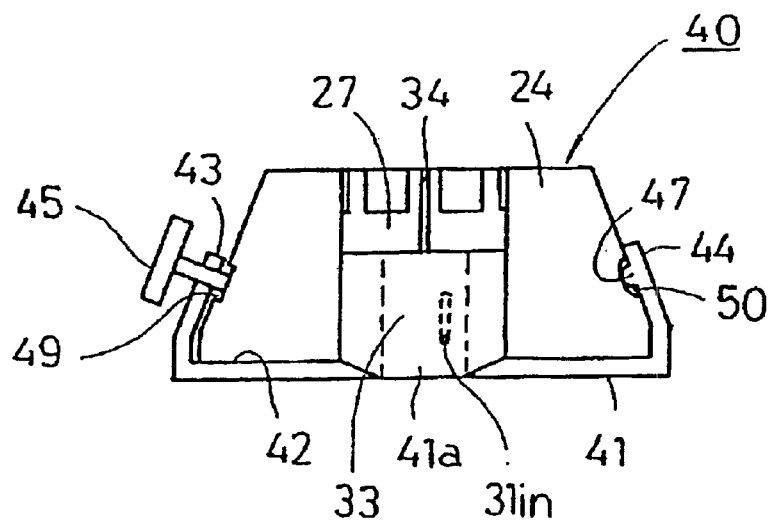
FIG. 8 represents a cross section along the line A—A in FIG. 7.
Figure 9:
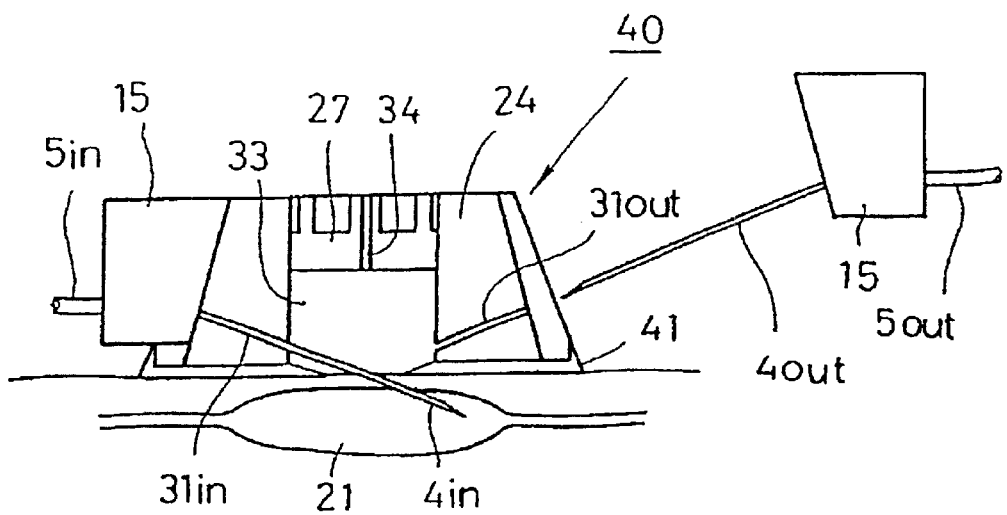
FIG. 9 represents a cross section along the line B—B in FIG. 7.
Figure 10:
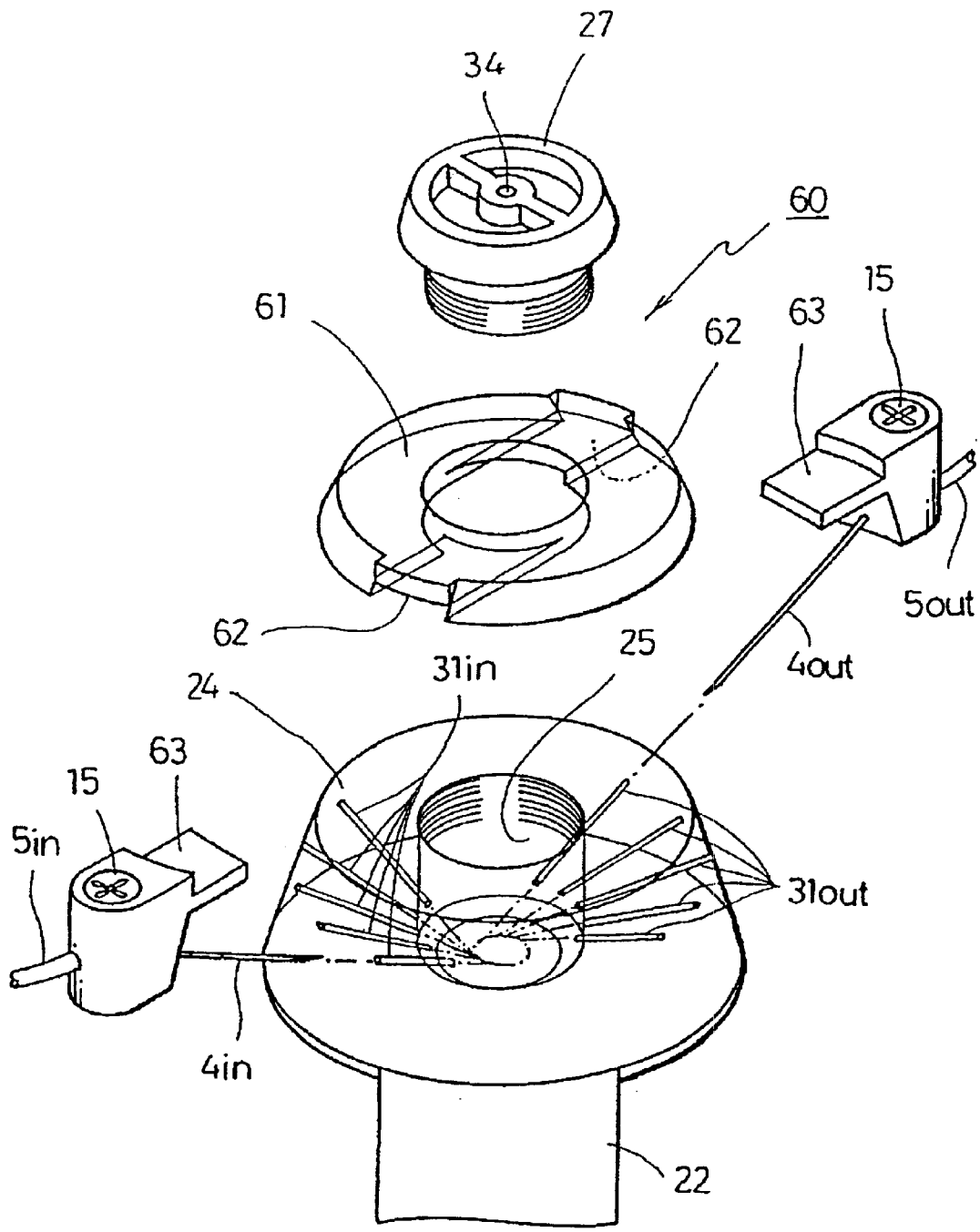
FIG. 10 represents an exploded assembly diagram showing yet another mode of embodiment of the insertion guide.
Figure 11:
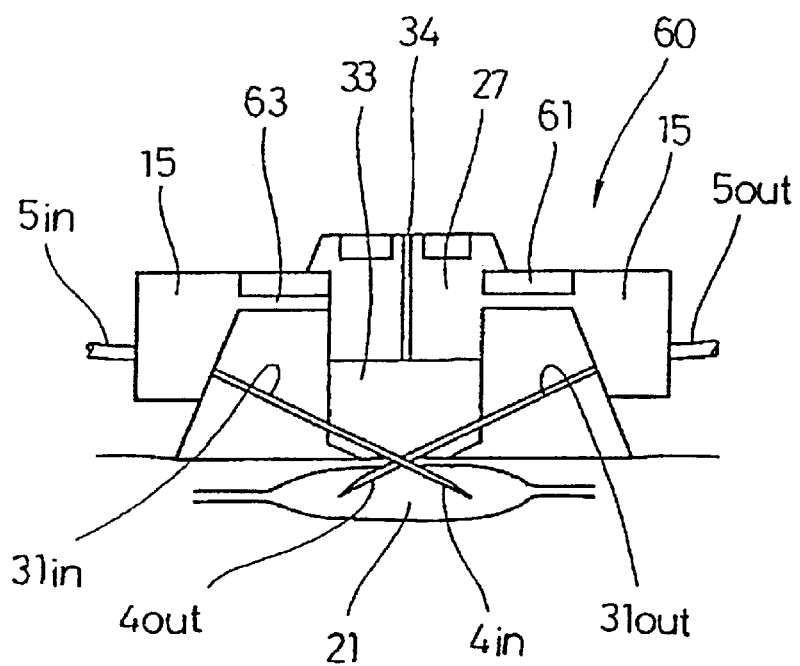
FIG. 11 represents a cross section thereof.
Figure 12:
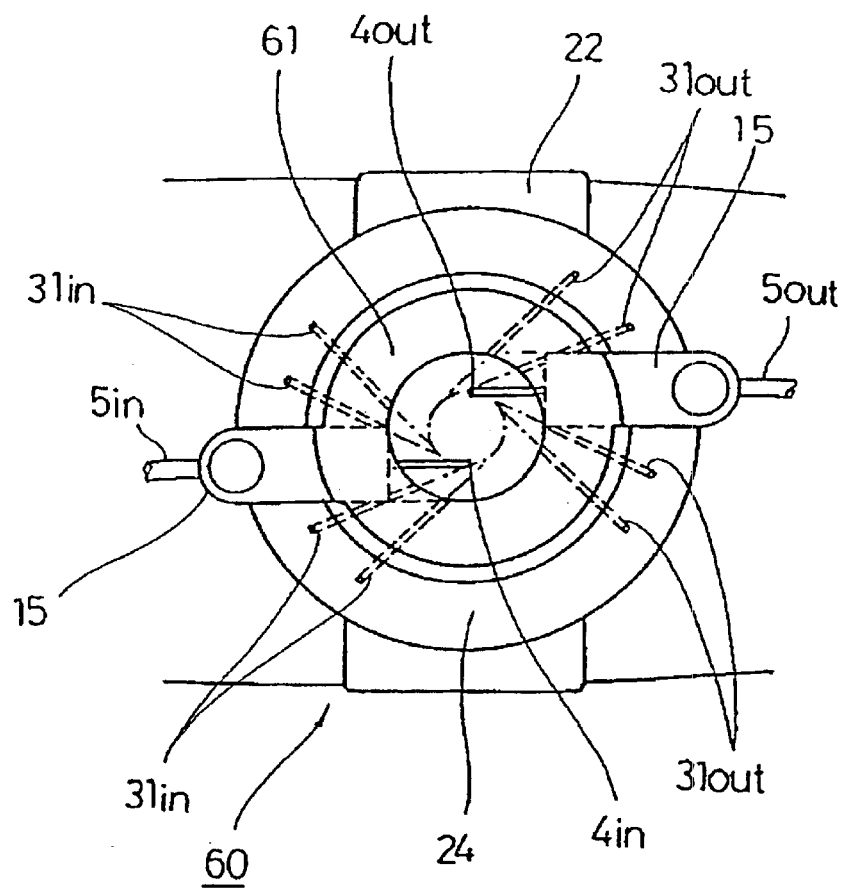
FIG. 12 represents a plan view thereof.

FIG. 1 is a fluid circuit diagram showing one example of an artificial kidney according to the present invention, FIG. 2 is a figure showing the state in which it is used, FIG. 3 is an exploded assembly diagram showing an insertion guide used therein, FIG. 4 is a figure showing the insertion guide fitted to the arm, FIG. 5 is an explanatory figure showing the state in which it is used, FIG. 6 is an exploded assembly diagram showing another mode of embodiment of the insertion guide, FIG. 7 is a plan view thereof, FIG. 8 is a cross section along the line A—A in FIG. 7, FIG. 9 is a cross section along the line B—B in FIG. 7, FIG. 10 is an exploded assembly diagram showing yet another mode of embodiment of the insertion guide, FIG. 11 is a cross section thereof, and FIG. 12 is a plan view thereof.

The artificial kidney 1 in this example is of a portable type which is fitted to the body, and a circulatory system 3 outside the body, which purifies the blood and returns it into the body again, is formed in a portable unit 2 which can be fitted to the body.

This portable unit 2 can be one in which a frame, on which the circulatory system 3 outside the body is formed, is fitted to the body using a belt or the like, or can be one in which the circulatory system 3 outside the body is formed in or on a robust fabric or leather jacket.

In the circulatory system 3 outside the body, a blood inflow tube 5in, which has attached to its front end an arterial needle 4in which takes blood from inside the body, is connected to a filtration device 6 which filters the blood and extracts, in the form of initial urine, a water fraction containing waste materials.

Formed in the filtration device 6 are an initial urine extraction port 6a where the initial urine which has passed through a filtration membrane 6F is extracted, and a blood outlet port 6b from which flows the blood from which the initial urine has been eliminated and which contains many blood constituents which have not passed through the filtration membrane 6F; and the above mentioned initial urine extraction port 6a is connected to a distillation device 7, while the above mentioned blood outlet port 6b is connected to a mixing chamber 12a of a purified blood mixing device 10 which is discussed hereinbelow.

The distillation device 7 comprises a heating chamber 7A where the initial urine supplied from the filtration device 6 is heated or the like and the water fraction is evaporated, a condensation device 7B where the evaporated water fraction is condensed and cooled to a predetermined temperature, and a distilled water storage chamber 7C where the distilled water which is recovered accumulates.

It will be noted that the heating chamber 7A and the condensation device 7B are covered on their outsides with insulating materials in order to improve thermal efficiency, and the arrangement is such that the heat on the inside of the heating chamber 7A does not leak to the outside, and the cold air on the inside of the condensation device 7B does not leak to the outside.

Also, the heating chamber 7A is connected to an excretion bag 9 via a fixed-rate pump 8 which discharges the initial urine, in which waste materials have been concentrated, at a predetermined flow rate (e.g. 2 to 4 cc/min), and the distilled water storage chamber 7C is connected to the purified blood mixing device 10.

In this purified blood mixing device 10, the mixing chamber 12a of a fixed-rate bellows pump (pressure forwarding pump) 12 worked by a compressor 11 has connected to it the blood outlet port 6b of the above mentioned filtration device 6, the above mentioned distilled water storage chamber 7C, and a dialysis source-fluid bag 13 containing a 35 times concentrate commercial dialysis source fluid constituting a concentrated replenishing fluid; and has connected to it a blood flow-back tube 5out on the front end of which is attached a venous needle 4out.

Also, the arrangement is such that dialysis source fluid supplied to the mixing chamber 12a from the dialysis source-fluid bag 13 is diluted 35 times by the distilled water supplied from the distilled water storage chamber 7C, and the resultant fluid is mixed with the blood supplied from the blood outlet port 6b of the filtration device 6 before being returned into the body via the blood flow-back tube 5out.

It will be noted that blood flow monitors 15 each equipped with a bladed wheel rotated by the blood flow are fitted to the blood inflow tube 5in and the blood flow-back tube 5out.

Further, the blood inflow tube 5in is formed with an injection port (not depicted) connected to a cylinder pump or the like which automatically injects a blood anticoagulant such as heparin, and the blood flow-back tube 5out is formed with an injection port (not depicted) connected to a cylinder pump or the like which automatically injects a drug such as protamine which cancels out the effects of the blood anticoagulant and restores the blood clotting action.

Also, the blood outlet port 6b of the filtration device 6 is formed with a blood extraction port (not depicted) which supplies blood to a biochemical monitor which analyses factors such as the constituents of the blood.

Further, the filtration device 6 has the ability to filter between 80 and 150 cc/min of blood taken from inside the body and to discharge between 20 and 40 cc/min of initial urine, while the above mentioned distillation device 7 has the ability to distil the initial urine and recover between 18 and 36 cc/min of distilled water, and to discharge between 2 and 4 cc/min of the initial urine in which waste materials have been concentrated.

Although not depicted, the portable unit 2 is fitted with a controller which controls the pumps 8 and 12 and the distillation device 7, and with any necessary batteries, and each flow circuit is provided with, by way of example, a flow-rate-regulating valve and/or a non-return valve as required.

Further, the arterial needle 4in and the venous needle 4out are inserted into fistulae 21A and 21B termed AVFs, which are formed on the upstream side and the downstream side of a vein V running beneath the skin of the arm, by means of an insertion guide 20 shown in FIG. 3 to FIG. 5.

The insertion guide 20 comprises a ring-shaped holder 24 fitted to, by way of example, the inside of the forearm 23 by means of a belt 22 using a flat-plane fastener such as Magic Tape (brand name); a pressure-contacting element (haemostatic body) 26 inserted into a through-hole 25 formed in the middle of the said holder 24 and placed fast against the skin in such a way as to cover the above mentioned two fistulae 21A and 21B; and a clamping screw 27 which presses the pressure-contacting element 26 towards the skin.

The pressure-contacting element 26 is arranged in such a way that a pair of keys 28 and 28 are formed in its diametral direction and engage with key channels 29, 29 or 30, 30 formed in the through-hole 25 of the holder 24.

The depths of the key channels 29 and 30 differ from each other, and one set of key channels 29 and 29 is formed to a depth such that, when the keys 28 and 28 of the pressure-contacting element 26 are inserted and the clamping screw 27 is tightened, the lower-end surface stops at a position which coincides with the lower-end surface of the holder 24 as shown in FIG. 5(a).

Further, the other set of key channels 30 and 30 is formed to a depth such that, when the keys 28 of the pressure-contacting element 26 are inserted and the clamping screw 27 is tightened, the lower-end surface stops at a position projecting proud of the lower-end surface of the holder 24 as shown in FIG. 5(b).

Also, the holder 24 and the pressure-contacting element 26 are formed with a canalicular arterial guide hole 31in which guides the arterial needle 4in, and a canalicular venous guide hole 31out which guides the venous needle 4out, in such a way as to run through them when the keys 28 and 28 of the pressure-contacting element 26 have been engaged with the one set of key channels 29 and 29 and the clamping screw 27 has been tightened.

The arterial guide hole 31in is formed in such a way as to guide the arterial needle 4in downwards at an incline from the shoulder side to the wrist side relative to the fistula 21A on the upstream side, while the venous guide 31out is formed in such a way as to guide the venous needle 4out downwards at an incline from the wrist side to the shoulder side relative to the fistula 21B on the downstream side, in the opposite direction to the above mentioned arterial guide hole 31in.

Further, attached to the entrances of the guide holes 31in and 31out are stoppers 32 which secure, to the holder 24, the blood flow monitors 15 attached towards the rear ends of the needles 4in and 4out when the said needles 4in and 4out have been inserted into the fistulae 21A and 21B.

The stopper 32 is formed from a transparent plate or the like such that the rotation of the bladed wheel of the blood flow monitor 15 can be seen.

It will be noted that the needles 4in and 4out are selected to have a length such that, when they are inserted, the above mentioned blood flow monitors 15 abut against the holder 24 when the tips have reached the insides of the fistulae 21A and 21B.

Further, when the above mentioned needles 4in and 4out are withdrawn, the keys 28 and 28 of the pressure-contacting element 26 are made to engage with the other key channels 30 and 30 and the clamping screw 27 is tightened, the lower-end surface of the pressure-contacting element 26 projects downwards proud of the lower-end surface of the holder 24 and presses strongly on the skin, and thus insertion markings are inhibited and the blood is stopped after the needles 4in and 4out are withdrawn.

It will be noted that the pressure-contacting element 26 is coated on its lower end surface with a transparent silicone rubber or the like, and in the middle part thereof is placed an interchangeable sponge 33.

Further, there is formed a drug-supply flow-path 34 through which sterilizing solution, pain relieving agents or haemostatic agents are supplied to the sponge 33 from the obverse surface side of the holder 24, and soaked onto the skin.

By using this insertion guide 20, the needles 4in and 4out can be inserted simply and under more or less the same conditions whoever inserts them, without any lateral shaking since they are guided in the longitudinal direction along the guide holes 31in and 31out, both when they are being put in and when they are being withdrawn.

Further, since the needles 4in and 4out are secured inserted in the arm, the needles 4in and 4out will not be withdrawn even if they are moved somewhat.

Consequently, even when a thick needle of 16 gauge or less is used, the fistulae 21A and 21B, which have previously had a relatively short duration of use, can be used over a long period of time.

The above is one example of the configuration of the present invention, and its action is now described.

Firstly, the portable unit 2 is fitted to the body and the insertion guide 20 is secured to the arm, the arterial needle 4in and the venous needle 4out are respectively inserted into an upstream and a downstream fistula 21A and 21B, thereby connecting the circulatory system 3 outside the body to the blood vessels via the blood inflow tube 5in and the blood flow-back tube 5out.

In this case, the arterial needle 4in and the venous needle 4out are guided by the guide holes 31in and 31out in only the longitudinal directions thereof, and thus the needles 4in and 4out can be inserted simply and under more or less the same conditions by anybody, without any lateral shaking.

Also, blood at, for example, 125 cc/min is forwarded from the upstream fistula 21A, through the arterial needle 4in and the blood inflow tube 5in, and to the filtration device 6.

In the filtration device 6, the blood is filtered, a water fraction at 30 cc/min which passes through the filtration membrane 6F and contains waste materials is sent as initial urine from the initial urine extraction port 6a to the distillation device 7, and the remaining 95 cc/min of blood containing a blood fraction is sent from the blood outlet port 6b to the bellows pump 12.

In the distillation device 7, the initial urine sent from the filtration device 6 is distilled and, by way of example, distilled water is recovered at 28 cc/min, and 2 cc/min of initial urine in which waste materials have been concentrated is discharged at a constant rate to the excretion bag 9 by means of the fixed-rate pump 8.

Also, 0.8 cc/min of dialysis source fluid sent from the dialysis source-fluid bag 13 is diluted 35 times by the 28 cc/min of distilled water forwarded to the bellows pump 12 of the purified blood mixing device 10, and is mixed safely with 95 cc/min of blood forwarded from the blood outlet port 6b of the filtration device 6, which results in approximately 124 cc/min of purified blood which is returned into the body via the blood flow-back tube 5out.

More specifically, when the artificial kidney 1 of this example is used, the water fraction containing waste materials, in the blood from the body, is purified at 30 cc/min.

In this way, given that the blood filtration rate is 28 cc/min, it is possible to maintain a kidney performance approximately 25% of the filtration rate of 125 cc/min of healthy individuals, and this is believed to be on the same level as the kidney performance in patients undergoing dialysis in institutions such as dialysis centers attached to university hospitals and the like.

Moreover, since the dialysis source fluid to be supplied is at 0.8 cc/min, the maximum figure is 1.2 liters even if the blood is filtered continuously over 24 hours. Consequently, if the dialysis source-fluid bag 13 containing 300 cc is replaced every 5 to 6 hours, the dialysis source fluid can be supplemented.

Further, the initial urine in which waste materials have been concentrated by the distillation device 7 is discharged at a discharge rate of 2 cc/min into the excretion bag 9, and a 120 cc volume is stored in 1 hour, and thus should be excreted into the toilet or the like at predetermined times.

Also, when the purification of the blood has been completed, the needles 4in and 4out are taken out, the clamping screw 27 of the holder 24 is undone, the orientation of the pressure-contacting element 26 is changed, and, when the clamping screw 27 is tightened again, the lower end surface of the pressure-contacting element 26 projects proud below the lower end surface of the holder 24 and presses strongly against the skin, in addition to which the orientation differs from that when the needles 4in and 4out are put in, and thus insertion markings can be pressed by a portion where the guide holes 31in and 31out are not formed.

In this way a haemostatic effect can be effectively achieved even when using a thick needle.

Further, if required, the haemostatic effect will be enhanced if a haemostatic agent is supplied from the drug supply flow-path 34, since the haemostatic agent will soak out from the sponge 33 onto the skin.

It will be noted that the concentrated replenishing fluid is not limited to a commercial dialysis source fluid, and may be a fluid with a composition approaching the serum constituent which has been concentrated to a predetermined concentration.

Further, a description has been given of a portable artificial kidney 1 in which a circulatory system 3 outside the body has been formed in a portable unit 2, but the present invention can also be satisfactorily employed in a fixed-location artificial kidney in which the circulatory system outside the body is formed in an immobile unit of the bedside console type.

In this case as well, since the initial urine is distilled, it is sufficient to replenish dialysis source fluid at about 1.2 liters a day, and there is no need to use 150 to 200 liters of dialysis fluid or substantial amounts of replenishing fluid, and thus there is no need to manage the dialysis fluid/replenishing fluid and the device can be of reduced size, and blood can be purified in places such as the home and travel destinations without specialist staff.

Also, if the invention is employed in a fixed-location artificial kidney, a better purification ability is obtained than with a portable artificial kidney, and thus, for example, the blood can be purified while sleeping at home, and the blood can be purified to a formulation corresponding to the case particulars of the individual patient, and it goes without saying that there is no need to attend a medical institution in order to perform the dialysis.

FIG. 6 to FIG. 9 show another mode of embodiment of an insertion guide. It will be noted that parts which are common to FIG. 3 to FIG. 5 have been ascribed the same references, and detailed descriptions have been omitted.

The insertion guide 40 of this example has been arranged in such a way that the insertion direction of the needles 4in and 4out can be changed by changing the orientation of the guide holes 31in and 31out by rotating a holder 24 formed with an arterial guide hole 31in and a venous guide hole 31out.

The holder 24 is formed with an approximately frusto-conical shape, and is formed so as to be able to be rotated to left and right by having its floor surface 24a engage in a circular recess 42 of a base plate 41 secured to the arm by a belt 22 or the like.

The base plate 41 is formed with latching pieces 43 and 44, which are abutted against inclined surfaces of the holder 24, in facing positions in the diametral direction, and on one of the latching pieces 43 is formed a screw hole 46 into which is screwed a locking screw 45 for securing the holder 24, while on the inside of the other latching piece 44 is formed a projection 47.

It will be noted that the widths of the latching pieces 43 and 44 are formed so as to be no more than the widths of recessed channels 48in and 48out discussed hereinbelow.

Further, the holder 24 is formed with recessed channels 48in and 48out in which are opened the guide holes 31in and 31out discussed above, and respective blood flow monitors 15, to which the arterial needle 4in and the venous needle 4out are attached, are engaged in the said recessed channels 48in and 48out.

The guide holes 31in and 31out are formed in a direction tangential to a circle whose eccentricity is the radius, by way of example, in such a way that the above mentioned needles 4in and 4out can be inserted into a fistula 21 in positions biased from the centre of rotation thereof (see FIG. 7).

Also, the side surface 24b thereof is formed with positioning recesses 49 . . . and 50 . . . against which the above mentioned locking screw 45 and projection 47 abut, respectively in corresponding positions in the diametral direction, for example at 22.5° intervals within a range of 90°.

Also, firstly, after the recessed channels 48in and 48out of the holder 24 have been matched with the latching pieces 43 and 44 and the holder 24 has been fitted to the base plate 41, if the holder 24 is rotated while the locking screw 45 is in the loose state, then the projection 47 is positioned making a "clicking" sound every time it enters a positioning recess 50. Also, when the locking screw 45 is tightened, its front end abuts into the positioning recess 49 and the holder 24 is secured.

Next, a medical disinfectant sponge 33 or degreasing pad is put into the through hole 25 formed in the center of the holder 24, is clamped down by the clamping screw 27, and then the needles 4in and 4out are placed in the guide holes 31in and 31out and poked into them, whereupon the front ends pass through the through hole 41a of the base plate 41 and are inserted into the fistula 21.

By using this insertion guide 40, the needles 4in and 4out can be inserted simply and under more or less the same conditions whoever inserts them, without any lateral shaking since they are guided in the longitudinal direction along the guide holes 31in and 31out, both when they are being put in and when they are being withdrawn.

Further, assuming that on ordinary days blood purification is carried out daily, the holder 24 can be positioned by rotating in 22.5° increments, and needles 4in and 4out can be inserted in the same fistula 21 at different insertion points from different directions over 5 days.

Consequently, insertion at the same insertion point happens at weekly intervals, the burden placed on the skin is diminished, and the life of the fistula 21 can be extended.

Also, when the holder 24 is viewed from above, the angle of the needles 4in and 4out relative to the direction of flow of the blood flowing in the fistula 21 is set so as to be a maximum of 45°, and, when it is of this magnitude, there are no problems with introduction of blood from the arterial needle 4in and flow-back of blood from the venous needle 4out.

FIG. 10 to FIG. 12 show yet another mode of embodiment of an insertion guide according to the present invention, and parts common to FIG. 3 to FIG. 5 have been ascribed the same references and detailed explanation has been omitted.

The insertion guide 60 in this example has been arranged in such a way that the insertion direction of the needles 4in and 4out can be changed without rotating the holder 24: it is formed with a plurality of (e.g. 5) arterial guide holes 31in which guide the arterial needle 4in such that it can be inserted into different insertion points of the same fistula 21, and is formed with a plurality of (e.g. 5) venous guide holes 31out which guide the venous needle 4out such that it can be inserted into different insertion points of the same fistula 21, when the holder 24 has been fitted to the arm by means of a belt 22 or the like.

The respective guide holes 31in and 31out are formed in a radiating shape in directions tangential to a small-diameter hypothetical circle drawn on the fistula 21, in such a way that the above mentioned needles 4in and 4out can be inserted in different positions around the hypothetical circle.

Further, latching pieces 63 which are inserted into and latch with recessed channels 62 of a stopper 61 secured to the upper surface of the holder 24 are formed on the blood flow monitors 15 to which the needles 4in and 4out are attached.

Also, the holder 24 is secured to a predetermined position on the arm, a disinfectant sponge 33 or degreasing pad is put into the through hole 25, the stopper 61 is placed over the holder 24, and the clamping screw 27 is lightly tightened, in which state the needles 4in and 4out are poked in from predetermined guide holes 31in and 31out and inserted into the fistula 21, after which the latching pieces 63 of the blood flow monitors 15 and the recessed channels 62 of the stopper 61 are engaged with each other and the clamping screw 27 is tightened, whereupon the latching pieces 63 are pressed against the stopper 61 and the needles 4in and 4out are secured.

By using this insertion guide 60, the needles 4in and 4out can be inserted simply and under more or less the same conditions whoever inserts them, without any lateral shaking since they are guided in the longitudinal direction along their respective guide holes 31in and 31out, both when they are being put in and when they are being withdrawn.

Further, in this example too, if the guide holes 31in and 31out are changed every day, the needles 4in and 4out can be inserted into the same fistula 21 at different insertion points from different directions over 5 days.

Consequently, insertion at the same insertion point happens at weekly intervals, the burden placed on the skin is diminished, and the life of the fistula 21 can be extended.

As described above, when the artificial kidney of the present invention is employed, concentrated replenishing fluid is diluted with distilled water obtained by distilling initial urine, and the resulting fluid is mixed with the blood before flowing back into the body, and thus there are outstanding advantages in that it is sufficient to supplement about 1.2 liters of dialysis source fluid per day when using a commercial dialysis source fluid which has been concentrated 35 times as a concentrated replenishing fluid, and there is no need to replenish a substantial amount of replenishing fluid, and thus blood can be purified by the individual him or herself taking advantage of, for example, sleeping time, even in places such as the home or a travel destination.

Further, when an insertion guide according to the present invention is employed, because the arterial and the venous needles can be inserted simply and under more or less the same conditions whoever inserts them, without any lateral shaking since they are guided only in their longitudinal direction by the guide holes, both when they are being put in and when they are being withdrawn, it follows that there is the outstanding advantage that adverse effects on the skin and fistula due to insertion errors are reduced.

List of the Reference Numbers in the Drawings:
- 1—artificial kidney
- 2—portable unit
- 3—circulation system outside the body
- 4in—arterial needle
- 4out—venous needle
- 5in—blood inflow tube
- 5out—blood flow-back tube
- 6—filtration device
- 7—distillation device
- 10—purified blood mixing device
- 12—fixed-rate bellows pump (pressure forwarding pump)
- 20—insertion guide
- 21, 21A and 21B—fistulae
- 24—holder
- 26—pressure-contacting element (haemostatic body)
- 31in—arterial guide hole
- 31out—venous guide hole
- 32—stopper
- 34—drug-supply flow-path

What is claimed is:

1. Insertion guide for inserting an arterial needle, which takes blood out from the body, and a venous needle, which returns purified blood into the body, into at least one fistula formed in a vein running beneath the skin of the arm, the insertion guide comprising:
    a holder having an arterial guide hole, which guides the arterial needle downwards at an incline from a shoulder side of the arm to a wrist side of the arm relative to the fistula, and a venous guide hole, which guides the venous needle downwards at an incline from the wrist side to the shoulder side relative to the fistula; and
    a drug-supply flow-path for supplying one of a sterilizing solution, a pain relieving agent, and a haemostatic agent to the skin via one of the guide holes of the holder and a portion of the holder in a vicinity of the guide holes.

2. Insertion guide according to claim 1, wherein the holder comprises a through hole configured to receive a pressure-contacting element, and wherein the insertion guide further comprises clamping member configured to press the pressure-contacting element towards the skin.

3. Insertion guide according to claim 2, wherein the pressure-contacting element is receivable in the holder in one of a first position, in which a lower end surface of the pressure-contacting element coincides with a lower end surface of the holder, and a second position, in which the lower end surface of the pressure-contacting element projects with respect to the lower end surface of the holder.

4. Insertion guide according to claim 3, wherein the pressure-contacting element comprises a corresponding arterial guide hole and a corresponding venous guide hole, which in said first position of the pressure-contacting element are respectively aligned with the arterial guide hole and the venous guide hole of the holder.

5. Insertion guide according to claim 1, further comprising a stopper for securing the needles and the holder in a state in which the needles have been poked through the guide holes and their front ends have pierced the fistulae.

6. Insertion guide according to claim 1, further comprising a base plate securable to the arm, the holder being rotatably attached to the base plate.

7. Insertion guide according to claim 6, wherein the guide holes of the holder define needle insertion directions offset from the axis of rotation of the holder.

8. Insertion guide according to claim 1, wherein the holder comprises a plurality of arterial guide holes and venous guide holes.

9. Insertion guide according to claim 8, wherein the guide holes of the holder define needle insertion directions offset from the axis of rotation of the holder.

10. Insertion guide for inserting ah arterial needle, Which takes blood out from the body, and a venous needle, which returns purified blood into the body, into at least one fistula formed in a vein running beneath the skin of the arm, the insertion guide comprising:
    a holder having an arterial guide hole which guides the arterial needle downwards at an incline from a shoulder side of the arm to a Wrist side of the arm relative to the fistula, and a venous guide hole, which guides the venous needle downwards at an incline from the wrist side to the shoulder side relative to the fistula; and
    a stopper associated with said holder, the stopper being movable between an unlatched condition and a latched condition for securing the needles and the holder in a state in which the needles have been poked through the guide holes and their front ends have pierced the fistulae.

11. Insertion guide according to claim 10, further comprising a pressure-contacting element receivable into the holder in one of a first position, in which a lower end surface of the pressure-contacting element coincides With a lower end surface of the holder, and a second position, in which the lower end surface of the pressure-contacting element projects with respect to the lower end surface of the holder.

12. Insertion guide according to claim 11, wherein the pressure-contacting element comprises a corresponding arterial guide hole and a corresponding venous guide hole, which in said first position of the pressure-contacting element are respectively aligned with the arterial guide hole and the venous guide hole of the holder.

13. Insertion guide for inserting an arterial needle, which takes blood out from the body, and a venous needle, which returns purified blood into the body, into at least one fistula formed in a vein running beneath the skin of the arm, the insertion guide comprising:
    a holder having an arterial guide hole, which guides the arterial needle downwards at an incline from a shoulder side of the arm to a wrist side of the arm relative to the fistula, and a venous guide hole, which guides the venous needle downwards at an incline from the Wrist side to the shoulder side relative to the fistula; and
    a base plate securable to the arm, the holder being rotatably attached to the base plate.

14. Insertion guide according to claim 13, wherein the guide holes of the holder define needle insertion directions offset from the axis of rotation of the holder.

15. Insertion guide for inserting an arterial needle, which takes blood out from the body, and a venous needle, which returns purified blood into the body, into at least one fistula formed in a vein running beneath the skin of the arm, the insertion guide comprising:

a holder having a plurality of arterial guide holes, which guide the arterial needle downwards at an incline from a shoulder side of the arm to a wrist side of the arm relative to the fistula, and a plurality venous guide holes, which guide the venous needle downwards at an incline from the wrist side to the shoulder side relative to the fistula.

16. Insertion guide according to claim 15, wherein the guide holes of the holder define needle insertion directions offset from the axis of rotation of the holder.

\* \* \* \* \*

UNITED STATES PATENT AND TRADEMARK OFFICE
CERTIFICATE OF CORRECTION

PATENT NO. : 6,579,265 B1  
DATED : June 17, 2003  
INVENTOR(S) : Kazuhiko Kihara et al.

It is certified that error appears in the above-identified patent and that said Letters Patent is hereby corrected as shown below:

Column 12,  
Line 25, "ah" should read -- an --.  
Line 25, "Which" should read -- which --.  
Lines 32 and 64, "Wrist" should read -- wrist --.  
Line 45, "With" should read -- with --.

Column 14,  
Line 2, "plurality venous" should read -- plurality of venous --.

Signed and Sealed this

Sixteenth Day of September, 2003

JAMES E. ROGAN  
*Director of the United States Patent and Trademark Office*